United States Patent
Sim et al.

(10) Patent No.: US 11,193,100 B2
(45) Date of Patent: Dec. 7, 2021

(54) METHOD FOR CARBON RESOURCE UTILIZATION

(71) Applicant: Korea University Research and Business Foundation, Seoul (KR)

(72) Inventors: Sang Jun Sim, Seoul (KR); Byung Sun Yu, Cheonan-si (KR); Min Eui Hong, Seongnam-si (KR)

(73) Assignee: Korea University Research and Business Foundation, Seoul (KR)

(*) Notice: Subject to any disclaimer, the term of this patent is extended or adjusted under 35 U.S.C. 154(b) by 123 days.

(21) Appl. No.: 16/658,454

(22) Filed: Oct. 21, 2019

(65) Prior Publication Data

US 2020/0239913 A1 Jul. 30, 2020

(30) Foreign Application Priority Data

Jan. 25, 2019 (KR) .......... 10-2019-0009785

(51) Int. Cl.
*C12M 1/00* (2006.01)
*C12P 3/00* (2006.01)

(52) U.S. Cl.
CPC .............. *C12M 21/02* (2013.01); *C12P 3/00* (2013.01)

(58) Field of Classification Search
None
See application file for complete search history.

(56) References Cited

U.S. PATENT DOCUMENTS

2008/0087165 A1* 4/2008 Wright ............... B01D 53/04
95/51
2015/0072391 A1* 3/2015 Lam ............... C12Y 102/01005
435/165

FOREIGN PATENT DOCUMENTS

KR 10-2018-0000427 A 1/2018

OTHER PUBLICATIONS

Ramanan et al., Enhanced algal CO2 sequestration through calcite deposition by *Chlorella* sp. and Spirulina platensis in a mini-raceway pond, 2010, Bioresource Technology 101 (Year: 2010).*
Dhami et al., Application of calcifying bacteria for remediation of stones and cultural heritages, 2014, Frontiers in Microbiology (Year: 2014).*
Jakob et al., Cultivation of Emiliania huxleyi for coccolith production, 2018, Alga Research (Year: 2018).*
Addadi et al., Control of biogenic nanocrystal formation in biomineralization, 2016, Israel Journal of Chemistry (Year: 2016).*
Li et al., Role of Fungi in the Formation of Patinas on Feilaifeng Limestone, China, 2018, Environmental Microbiology (Year: 2018).*

(Continued)

*Primary Examiner* — Holly Kipouros
(74) *Attorney, Agent, or Firm* — NSIP Law

(57) ABSTRACT

A method for carbon resource utilization is disclosed. According to one embodiment, the method includes (a) supplying carbon dioxide to a medium to form bicarbonate ions ($HCO_3^-$) (S100), (b) inoculating one or more microalgal species into the medium, followed by photo-culture (S200), and (c) supplying calcium ions ($Ca^{2+}$) to the medium, where the microalgal species are photo-cultured, to produce calcite ($CaCO_3$)-containing biomass (S300).

13 Claims, 6 Drawing Sheets

(56) References Cited

OTHER PUBLICATIONS

Dittrich et al., Induced Calcite Precipitation by Cyanobacterium Synechococcus, 2003, Acta hydrochim. hydrobiol. (Year: 2003).*
Santomauro, Giulia, et al. "Formation of calcium carbonate polymorphs induced by living microalgae." *Journal of Biomaterials and Nanobiotechnology*, vol. 3, No. 4, Oct. 2012 (pp. 413-420).
Zhu, Chenba, et al. "A recycling culture of Neochloris oleoabundans in a bicarbonate-based integrated carbon capture and algae production system with harvesting by auto-flocculation." *Biotechnology for biofuels*, vol. 11, Issue 1, Dec. 1, 2018 (pp. 1-11).
Korean Office Action dated Oct. 10, 2019 in counterpart Korean Patent Application No. 10-2019-0009785 (6 pages in Korean).
Yoon, Se Young, et al., "Enhanced biodiesel production in Neochloris oleoabundans by a semi-continuous process in two stage photobioreactors." *Bioprocess and biosystems engineering*, vol. 38, No. 7, 2015 (pp. 1415-1421).
Korean Notice of Allowance dated Oct. 16, 2020 in counterpart Korean Patent Application No. 10-2019-0009785 (3 pages in Korean).

* cited by examiner (a)            (b)

METHOD FOR CARBON RESOURCE UTILIZATION

CROSS-REFERENCE TO RELATED APPLICATIONS

This application claims the benefit under 35 USC § 119(a) of Korean Patent Application No. 10-2019-0009785 filed on Jan. 25, 2019 in the Korean Intellectual Property Office, the entire disclosure of which is incorporated herein by reference for all purposes.

BACKGROUND OF THE INVENTION

1. Field of the Invention

The present invention relates to a method for carbon resource utilization, and more specifically to a biological hybrid system for carbon resource utilization that uses a combination of a biomass production process and a mineralization process based on microalgae.

2. Description of the Related Art

The phenomenon of global warming caused by large scale greenhouse gas emissions arising from the use of fossil fuels poses a threat to all living organisms on Earth, including human beings. Under these circumstances, carbon capture and sequestration (CCS) technologies for carbon dioxide reduction are actively being developed around the world. CCS technologies refer to methods in which a large amount of carbon dioxide released from a variety of sources, including thermal power plants, is concentrated, captured, and injected into the underground or deep ocean to isolate it from the atmosphere. CCS technologies are effective in reducing a large amount of carbon dioxide in a short time but the problems of unstable storage, difficult location selection, and high installation cost make CCS technologies substantially difficult to realize. Thus, carbon capture and utilization (CCU) technologies for directly utilizing carbon dioxide in industrial applications or converting carbon dioxide into high value-added materials rather than sequestering carbon dioxide have recently received more attention than CCS technologies. Particularly, biological processes for carbon dioxide conversion utilizing microalgae, photosynthetic microorganisms, have attracted attention as economical techniques that enable the production of various high value-added materials, such as biofuels, bioplastics, and biopharmaceuticals, simultaneously with carbon dioxide reduction. Microalgae, called phytoplanktons, are underwater unicellular organisms that photosynthesize. Microalgae are of increasing interest as highly potential biomass resources due to their ability to produce energy and industrial materials and reduce greenhouse gases. In the future, the utility value of microalgae is expected to rise in industrial fields, particularly energy, chemical, and environmental fields, for the following reasons.

First, in the energy field, microalgae have the highest oil productivity among all biodiesel producing crops. Soybean, canola, sunflower, oil palm, etc. have cultivation cycles of 4-8 months whereas microalgae can be cultivated on a daily basis due to their ability to proliferate several times in a day. The annual oil production from microalgae is at least 100 times that from soybean because microalgae have a higher fat content per unit weight. In addition, microalgae are bioresources free from the criticism that food resources are converted into energy and can produce biofuels with similar physical properties to petroleum diesel.

Second, in the chemical field, microalgae can produce numerous useful substances. Microalgae have been industrialized mainly in the field of food at present and will be industrialized in a wide range of applications, such as biochemicals and bioplastics, in the future. Health functional foods produced using *Chlorella, Spirulina,* and *Chlamydomonas,* which are microalgal species rich in protein, as well as *Haematococcus* that produces astaxanthin as a high value-added substance are currently commercially available to supplement various amino acids, antioxidants, and fatty acids.

Third, in the environmental field, microalgae have attracted the greatest attention due to their ability to reduce carbon dioxide, as described above, and their related studies have been continuously conducted all over the world. Microalgae can absorb carbon dioxide in an amount about twice the weight of biomass, which corresponds to a 10-50 times higher absorption efficiency than that of terrestrial plants. In addition, microalgae can be cultivated irrespective of specific soil and water quality. Related companies are extending the trials to utilize microalgae for carbon dioxide reduction and industrial wastewater purification.

Nevertheless, biological processes have the limitation of low $CO_2$ reduction rate per unit area in view of their characteristics. Biomass production processes based on microalgae need to be improved in terms of carbon dioxide reduction capacity, particularly in companies emitting large amounts of greenhouse gases that are obliged to treat a large amount of carbon dioxide. Thus, there is an urgent need for a solution to the disadvantages of biomass production processes.

SUMMARY OF THE INVENTION

The present invention has been made in an effort to solve the problems of the prior art, and it is one aspect of the present invention to provide an extended biological method for carbon resource utilization that uses a combination of a biomass production process and a mineralization process based on microalgae.

A method for carbon resource utilization according to one embodiment of the present invention includes (a) supplying carbon dioxide to a medium to form bicarbonate ions ($HCO_3^-$), (b) inoculating one or more microalgal species into the medium, followed by photo-culture, and (c) supplying calcium ions ($Ca^{2+}$) to the medium, where the microalgal species are photo-cultured, to produce calcite ($CaCO_3$)-containing biomass.

In the method for carbon resource utilization, the calcium ions are bound to the cell walls of the microalgal cells and react with the bicarbonate ions to produce calcite, and the microalgal cells adhere to one another through nonpolar covalent bonds between the calcite particles to produce biomass.

The method for carbon resource utilization may further include supplying a basic solution to the medium to maintain the pH of the medium at 7.0 to 8.5 between steps (a) and (b).

In the method for carbon resource utilization, the basic solution may be an 8 to 10 mM aqueous potassium hydroxide (KOH) solution.

The method for carbon resource utilization may further include primarily supplying a basic solution to maintain the pH of the medium at 7.5 to 8.5 such that biomineralization is induced, after supply of the calcium ions in step (c).

In the method for carbon resource utilization, the basic solution may be a solution of at least one base selected from the group consisting of sodium hydroxide (NaOH), potassium hydroxide (KOH), ammonia ($NH_4OH$), calcium hydroxide ($Ca(OH)_2$), and magnesium hydroxide ($Mg(OH)_2$).

In the method for carbon resource utilization, the microalgal species may be selected from the group consisting of *Chlorella vulgaris*, *Chlorella sorokiniana*, *Spirurlina* sp., *Dunaliella* sp., *Haematococcus pluvialis*, *Schizochytrium* sp., *Crypthecodinium* sp., *Chlamydomonas* sp., *Neochloris* sp., *Aphanizomenon* sp., and *Cyanobacterium* sp.

The method for carbon resource utilization may further include stopping the supply of the carbon dioxide to flocculate and collect the biomass after step (c).

In the method for carbon resource utilization, the calcium ions may be supplied by adding an aqueous calcium chloride ($CaCl_2$) solution to the medium.

In the method for carbon resource utilization, the aqueous calcium chloride solution may have a concentration of 0.03 to 0.06 M.

In the method for carbon resource utilization, the primarily supplied basic solution may be an aqueous potassium hydroxide (KOH) solution having a concentration not higher than 20 mM.

The method for carbon resource utilization may further include secondarily supplying another basic solution to induce both biomineralization and chemical mineralization after the primary supply of the basic solution.

In the method for carbon resource utilization, the secondarily supplied basic solution may be an aqueous potassium hydroxide (KOH) solution having a concentration not higher than 40 mM.

In the method for carbon resource utilization, step (c) may be carried out when the microalgal species are photo-cultured to a density of at least 1.0 g/l.

In the method for carbon resource utilization, the calcite may be in the form of nanoparticles.

The features and advantages of the present invention will become apparent from the following description with reference to the accompanying drawings.

Prior to the detailed description of the invention, it should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method.

The method of the present invention uses a combination of a microalgal culture process and a biological and/or chemical mineralization process to produce calcite as well as biomass, contributing to a significant reduction in the amount of carbon dioxide in an economical manner In addition, covalent bonding between calcite particles leads to an increase in the weight of microalgae. Therefore, biomass is allowed to flocculate by stopping the supply of carbon dioxide, with the result that the biomass can be easily collected without additional energy consumption.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
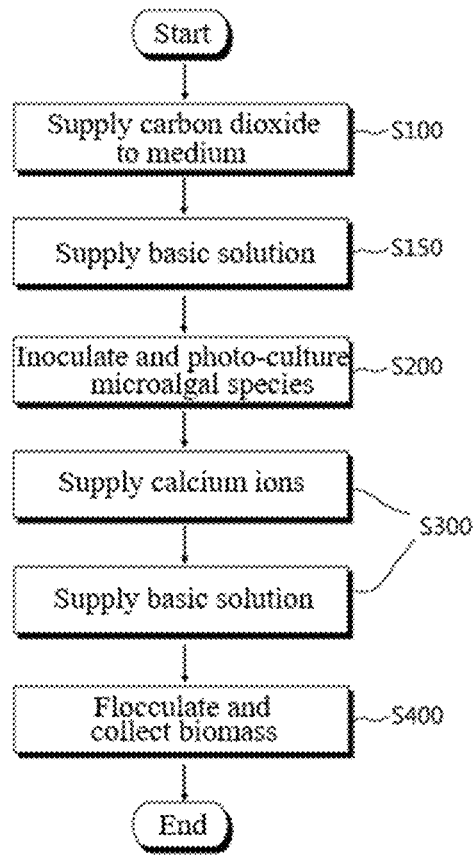
FIG. 1 is a flowchart showing a method for carbon resource utilization according to one embodiment of the present invention.

Other objects, advantages, and novel features of the invention will become more apparent from the following detailed description and preferred embodiments with reference to the appended drawings. In the drawings, the same elements are denoted by the same reference numerals even though they are depicted in different drawings. Although such terms as "first" and "second," etc. may be used to describe various elements, these elements should not be limited by above terms. These terms are used only to distinguish one element from another. In the description of the present invention, detailed explanations of related art are omitted when it is deemed that they may unnecessarily obscure the essence of the present invention.

Preferred embodiments of the present invention will now be described in detail with reference to the accompanying drawings.

FIG. 1 is a flowchart showing a method for carbon resource utilization according to one embodiment of the present invention.

As shown in FIG. 1, the method for carbon resource utilization includes (a) supplying carbon dioxide to a medium to form bicarbonate ions ($HCO_3^-$) (S100), (b) inoculating one or more microalgal species into the medium, followed by photo-culture (S200), and (c) supplying calcium ions ($Ca^{2+}$) to the medium, where the microalgal species are photo-cultured, to produce calcite ($CaCO_3$)-containing biomass (S300).

According to the method of the present invention, the use of microalgae enables the production of biomass while reducing a large amount of carbon dioxide, and at the same time, hard calcite is produced through calcium ion-mediated mineralization in an induction stage for high lipid accumulation so that the reduction rate of carbon dioxide can be markedly increased and concomitantly the content of lipids in biomass can be significantly increased. Conventional carbon capture and sequestration (CCS) technologies for carbon dioxide reduction are substantially difficult to realize due to the problems of unstable storage, difficult location selection, and high installation cost. Thus, carbon capture and utilization (CCU) technologies for directly utilizing carbon dioxide in industrial applications or converting carbon dioxide into high value-added materials rather than sequestering carbon dioxide have recently received more attention than CCS technologies. However, biological processes for carbon dioxide conversion utilizing microalgae, photosynthetic microorganisms, still have the problem of low carbon dioxide reduction rate and require an improvement in the ability of microalgae to reduce carbon dioxide for the treatment of a large amount of carbon dioxide. The present invention has been proposed as a solution to the above problems.

Specifically, the method for carbon resource utilization according to the present invention includes supply of carbon dioxide (S100), inoculation and photo-culture of one or more microalgal species (S200), and supply of calcium ions (S300).

In S100, carbon dioxide is supplied to a medium. Here, the medium may be accommodated in a reactor and supplied with carbon dioxide by aeration. The carbon dioxide supplied to the medium reacts with water to form bicarbonate ions ($HCO_3^-$) and hydrogen ions.

Next, in S200, one or more microalgal species are inoculated into the medium supplied with the carbon dioxide, followed by photo-culture. The microalgal species are underwater unicellular organisms that photosynthesize. In the present invention, the microalgal species may be selected from the group consisting of *Chlorella vulgaris, Chlorella sorokiniana, Spirurlina* sp., *Dunaliella* sp., *Haematococcus pluvialis, Schizochytrium* sp., *Crypthecodinium* sp., *Chlamydomonas* sp., *Neochloris* sp., *Aphanizomenon* sp., and *Cyanobacterium* sp. The inoculated microalgal species are photo-cultured in the medium. As the photo-culture proceeds, lipids are highly accumulated in the microalgal species. Hereinafter, this process is referred to as an induction stage for high lipid accumulation. The microalgal culture leads to the reduction of the carbon dioxide.

Before inoculation of the microalgal species, a basic solution may be supplied to the medium (S150). The basic solution serves to increase the alkalinity of the medium. The increased alkalinity ensures effective photo-culture of the microalgal species and allows the bicarbonate ions to maintain their ionic state. The basic solution is supplied in an amount such that the pH of the medium is maintained at 7.0 to 8.5, preferably 7.5 to 8.0. As the alkalinity of the medium increases, the productivity of calcite is improved without any significant influence on the final biomass, resulting in a remarkable increase in the removal rate of carbon dioxide.

The basic solution may be a solution of at least one base selected from the group consisting of sodium hydroxide (NaOH), potassium hydroxide (KOH), ammonia ($NH_4OH$), calcium hydroxide ($Ca(OH)_2$), and magnesium hydroxide ($Mg(OH)_2$). For example, an aqueous potassium hydroxide (KOH) solution having a concentration of 8 to 10 mM may be supplied to the medium to adjust the pH of the medium to the desired level. However, the kind and concentration of the basic solution are not necessarily limited to those mentioned above and may also be determined by collectively considering various factors such as the kinds of the microalgal species, the components of the medium, and the amount of the carbon dioxide supplied.

In the induction stage for high lipid accumulation through the microalgal photo-culture, calcium ions ($Ca^{2+}$) are supplied to the medium (S300). The calcium ions react with the bicarbonate ions to produce calcite ($CaCO_3$). S300 proceeds simultaneously with the microalgal photo-culture for biomineralization. Specifically, the calcium ions are bound to the negatively (−) charged cell walls of the microalgal cells and react with the dissolved bicarbonate ions to produce calcite ($CaCO_3$). Nonpolar covalent bonds are formed between the calcite particles. As a result, calcite-containing biomass is produced. The biomass has a structure in which the microalgal cells adhere to one another. The calcite may be in the form of nanoparticles. The calcite nanoparticles may have a size of 35 nm or less. Biomineralization refers to a process for conversion into a solid inorganic carbonate salt based on the use of carbonic anhydrase (CA), an enzyme found in microalgae. The enzyme CA functions as a catalyst for the reaction of carbon dioxide with water to form hydrogen ions and bicarbonate ions, and as a result, it activates the reaction of calcium ions with the bicarbonate ions to produce calcite.

The induction of calcium ion-mediated biomineralization in the induction stage for high lipid accumulation leads to an increased cell density, the growth of the microalgal species leads to carbon dioxide reduction, and the production of calcite contributes to further carbon dioxide reduction. Concomitantly, the content of lipids in biomass is increased significantly. For example, the lipids may be omega-3 fatty acids.

The calcium ions may be supplied, for example, by adding an aqueous calcium chloride ($CaCl_2$) solution to the medium. The aqueous calcium chloride solution has a concentration in the range of 0.01 to 0.07 M, preferably 0.03 to 0.06 M. Within this range, the above-described effects are pronounced.

The calcium ions are supplied when the microalgal species are photo-cultured to a density of at least 1.0 g/l in the induction stage for high lipid accumulation. For example, the calcium ions may be supplied when the microalgal species are photo-cultured to a density of about 1.0 to about 1.5 g/l. The reasons why calcium chloride is not added in the growth stage before the induction stage for high lipid accumulation are because the production of calcite makes it difficult to supply a sufficient amount of the calcium ions necessary for the growth of the microalgal species, damaging the growth of the microalgal species, and increases the turbidity of the medium to decrease the photosynthesis efficiency of the microalgal species, with the result that the growth of biomass may also be reduced.

The calcium ions, the bicarbonate ions, and the hydroxide ions are bonded to one another to produce calcite and water, resulting in a reduction in pH. The dissolved carbon dioxide is dissociated into bicarbonate and hydrogen ions that further reduce the pH to 3.0 to 4.5. Since biomineralization is effectively performed at a pH of 7.5 to 8.5, the basic solution is primarily supplied after supply of the calcium ions so that the pH of the medium can be maintained at 7.5 to 8.5. The basic solution may be a solution of at least one base selected from the group consisting of sodium hydroxide (NaOH), potassium hydroxide (KOH), ammonia ($NH_4OH$), calcium hydroxide ($Ca(OH)_2$), and magnesium hydroxide ($Mg(OH)_2$). For example, the primarily supplied basic solution may be an aqueous potassium hydroxide solution having a concentration of 20 mM or less.

The calcite is derived from biomineralization. In the present invention, after primary supply of the basic solution, another basic solution may be secondarily supplied to induce both biomineralization and chemical mineralization. Chemical mineralization refers to a process for converting carbon dioxide into a solid inorganic carbonate salt through a chemical reaction. According to chemical mineralization, calcium ions are supplied to liquefied carbon dioxide to produce calcite. That is, in the present invention, chemical mineralization is induced by supplying another basic solution at or above a level where biomineralization can be induced. The basic solution may be a solution of at least one base selected from the group consisting of sodium hydroxide (NaOH), potassium hydroxide (KOH), ammonia ($NH_4OH$), calcium hydroxide ($Ca(OH)_2$), and magnesium hydroxide ($Mg(OH)_2$). For example, the secondarily supplied basic solution may be an aqueous potassium hydroxide solution having a concentration of 40 mM or less. If the concentration exceeds 40 mM, the productivity of biomass is reduced. Thus, the concentration of the basic solution is preferably limited to 40 mM or less.

The resulting calcite-containing biomass can be flocculated and collected (S400). The nonpolar covalent bonds between the calcite particles in the biomass increase the total weight of cells. When the supply of carbon dioxide is stopped, the biomass is flocculated in a few minutes. Due to the increased weight, the biomass settles down and is separated from the medium. The separated biomass can be easily collected without the need for additional energy consumption.

The present invention will be more specifically explained with reference to the following examples, including evaluation examples.

EXAMPLE 1: CONSTRUCTION OF EXPERIMENTAL SETUP

Ten 500 ml graduated cylinders (width: 5 cm, height: 60 cm) were prepared to dissolve a large amount of carbon dioxide because general flasks can accommodate only a limited amount of dissolved carbon dioxide.

Each graduated cylinder was equipped with a versatile silicone stopper capable of closing the opening and through which gas injection and sampling could be done. Two Teflon tubes as gas and sampling lines were inserted into 2-3 mm holes formed in the stopper. The tubes were cut corresponding to the height of the graduated cylinder. A stone sparger for the supply of air containing 3% carbon dioxide was connected to the bottom end of the Teflon tube for gas supply.

EXAMPLE 2: MICROALGAL PHOTO-CULTURE

TAP-C was used as a medium. After 450 ml of the medium was introduced into each graduated cylinder, aeration was performed to inject carbon dioxide into the medium. A 9 mM aqueous KOH solution was introduced to increase the alkalinity of the medium. The pH of the medium was maintained between 7.5 and 8. *Neochloris oleoabundans* and *Chlorella sorokiniana* were used as microalgal species. Each of the microalgal species was inoculated at an initial density of 0.05 g/l, based on biomass. Light was irradiated at 300 $\mu E/m^2/s$ for 3 days. The final culture volume was adjusted to 500 ml.

EXAMPLE 3: COMBINATION OF BIOMASS PRODUCTION AND BIOMINERALIZATION IN INDUCTION STAGE

Five graduated cylinders were used for each strain. The microalgal species were mixed in a 5 liter-glass container equipped with a stopper capable of closing the opening such that their concentrations in the graduated cylinders were the same. The microalgal species (50 ml each) were further added. In the induction stage for lipid accumulation (that is, when each microalgal species was cultured to a density of 1.0-1.5 g/l), 0.02 M, 0.05 M, and 0.08 M aqueous $CaCl_2$ solutions were added to the different graduated cylinders. 1 ml of a 10 M aqueous KOH solution was supplied (that is, a 20 mM aqueous KOH solution was primarily supplied) to each graduated cylinder to maintain a pH of ≥7.5. Finally, calcite-containing biomass was produced.

EXAMPLE 4: INDUCTION OF BOTH BIOMINERALIZATION AND CHEMICAL MINERALIZATION

Another aqueous KOH solution was secondarily supplied to induce both biomineralization and chemical mineralization.

EXAMPLE 5: BIOMASS COLLECTION

Figure 2:
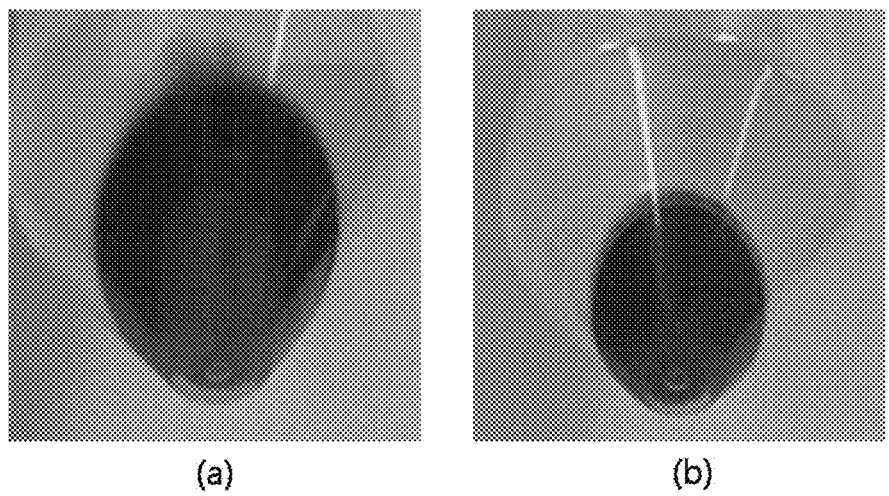
FIG. 2 shows images of flocculated biomass produced in Example 4 where a combination of biomass production and biomineralization processes was used and flocculated biomass produced in Comparative Example 1 where biomineralization was not induced.

FIG. 2 shows images of flocculated biomass produced in Example 4 where the combination of biomass production and biomineralization processes was used and flocculated biomass produced in Comparative Example 1 where biomineralization was not induced. Referring to (a) of FIG. 2, nonpolar covalent bonds between calcite particles on the cell walls of the microalgal cells increased the biomass weight. As soon as the aeration stopped, the biomass was separated from the medium by the density difference in a few minutes.

COMPARATIVE EXAMPLE 1

$CaCl_2$ was not added to one of the graduated cylinders and 0.02 M $CaCl_2$ and 1 mM acetazolamide (AZ) as a biomineralization inhibitor were added to another graduated cylinder. As a result, calcite-free biomasses were produced. The biomasses showed FAME contents similar to that of biomass where biomineralization was not induced.

COMPARATIVE EXAMPLE 2

As shown in (b) of FIG. 2, the biomass produced in Comparative Example 1 slowly settled down over time. Since the biomass was dispersed by stirring, an additional physico-chemical process was required to separate the biomass.

EVALUATION EXAMPLE 1: EVALUATION OF THE PRESENCE OR ABSENCE OF CALCITE

Figure 3A:
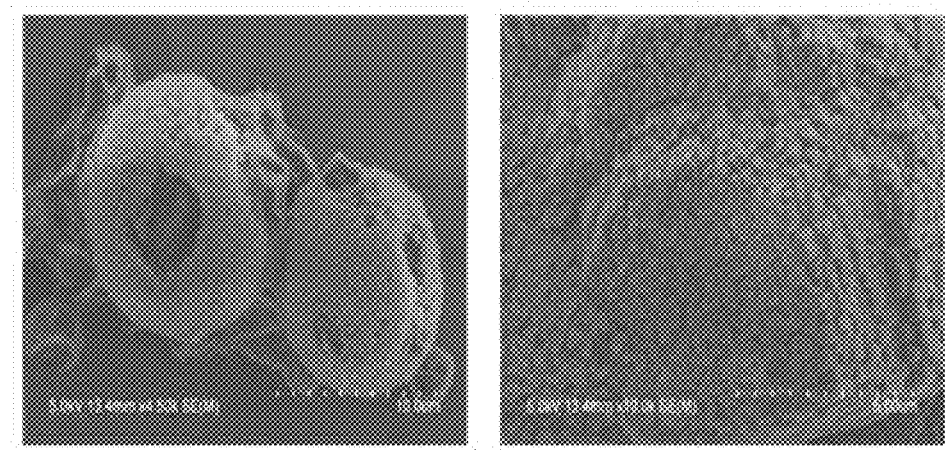
FIG. 3a shows scanning electron microscopy (SEM) images of biomass produced in Example 4.
Figure 3B:
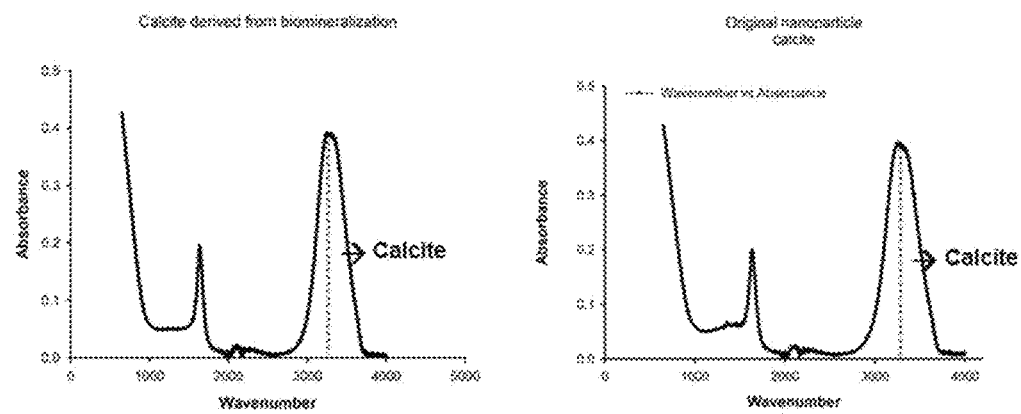
FIG. 3b shows the results of Fourier-transform infrared spectroscopy (FT-IR) for biomass produced in Example 4.
Figure 3C:
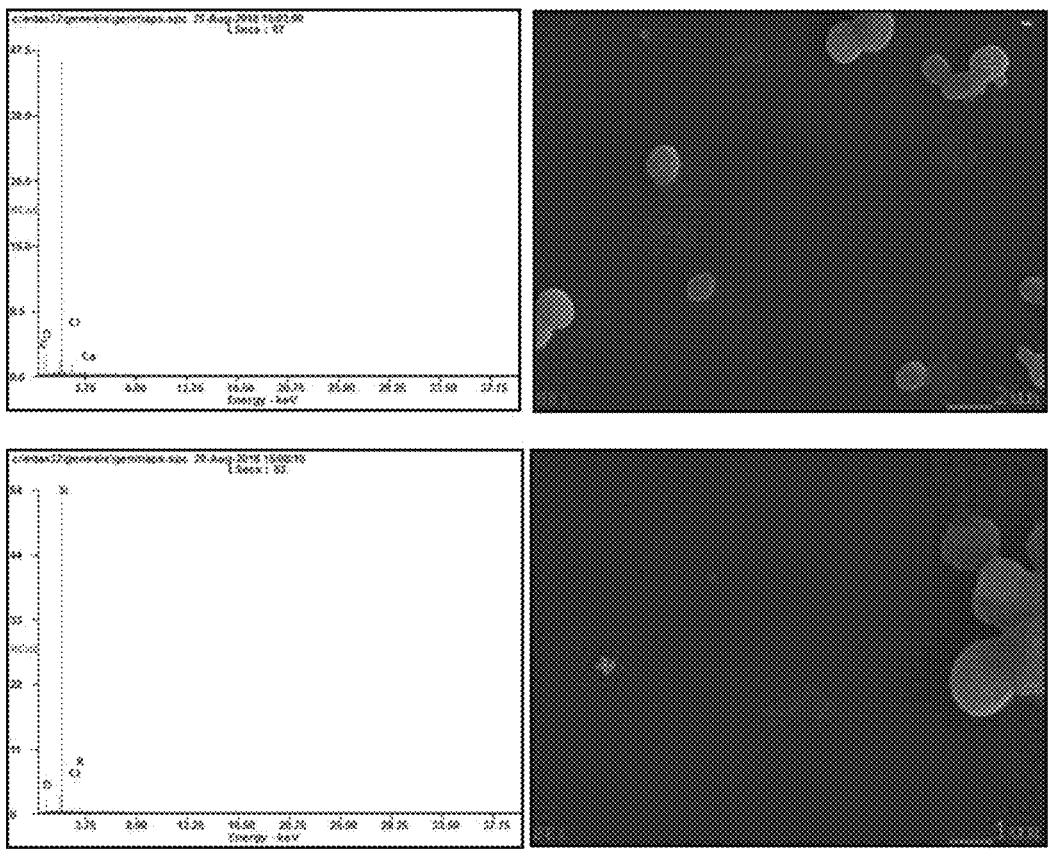
FIG. 3c shows the results of energy dispersive spectroscopy for biomass produced in Example 4 and an image of the biomass.

FIG. 3a shows scanning electron microscopy (SEM) images of the biomass produced in Example 4, FIG. 3b shows the results of Fourier-transform infrared spectroscopy (FT-IR) for the biomass produced in Example 4, and FIG. 3c shows the results of energy dispersive spectroscopy for the biomass produced in Example 4 and an image of the biomass.

A determination was made as to whether calcite was produced in the biomass collected in Example 4. The SEM images of FIG. 3a reveal the production of calcite. The FT-IR spectra of FIG. 3b reveal that calcite derived from biomineralization was the same as chemically synthesized nanoparticle calcite. FIG. 3c reveals that calcite particles were produced on the cell surfaces and calcite was not observed in areas other than the cell surfaces, demonstrating that the calcite was derived from biomineralization.

EVALUATION EXAMPLE 2: EVALUATION OF BIOMASS CONCENTRATIONS

Figure 4:
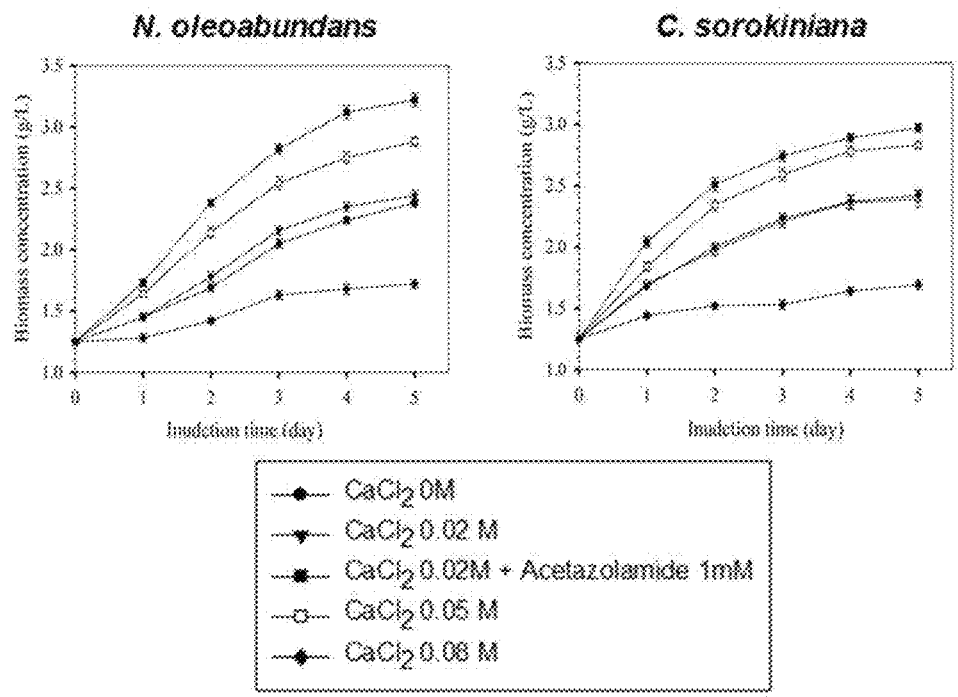
FIG. 4 shows the concentrations of biomasses produced in Example 3 and Comparative Example 1.

FIG. 4 shows the concentrations of the biomasses produced in Example 3 and Comparative Example 1.

Biomass and calcite coexisted in each of the samples of Example 3 and Comparative Example 1. The biomass and the calcite were quantified by the following procedure. First, the medium was removed from each sample (10 ml) using a centrifuge. Thereafter, the precipitate was washed three times with distilled water (pH 8) and centrifuged. 5 ml of the resulting precipitate containing both biomass and calcite was weighed. As for the remainder (5 ml), the supernatant was removed and 35 ml of distilled water whose pH was adjusted to ≤5 with HCl was added. The calcite was allowed to react with the hydrochloric acid with stirring for 30-60 sec. As a result of the reaction, $CaCl_2$ and carbon dioxide were recovered. The reaction mixture was centrifuged to remove the supernatant and the precipitate was washed with distilled water (pH 8) to remove calcite. The largest amount of the biomass was found to be present when 0.05 M $CaCl_2$ was added and the second largest amount of the biomass was found to be present when 0.02 M $CaCl_2$ was added. The amount of the biomass produced when 0.08 M $CaCl_2$ was added was smaller than that when $CaCl_2$ was not added. The biomass productivities when *Neochloris oleoabundans* was used were higher than those when *Chlorella sorokiniana* was used.

EVALUATION EXAMPLE 3: EVALUATION OF TOTAL CHLOROPHYLL CONTENTS

Figure 5:
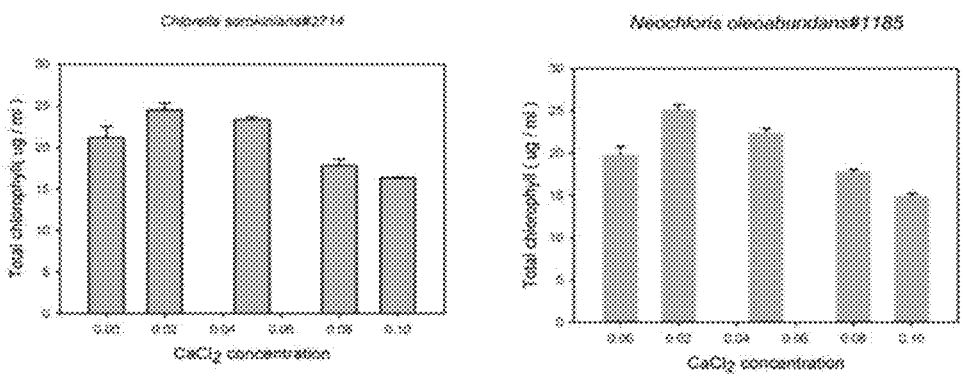
FIG. 5 shows the contents of total chlorophyll in biomasses produced in Example 3.

FIG. 5 shows the contents of total chlorophyll in the biomasses produced in Example 3.

The contents of total chlorophyll in the samples of Example 3 were measured. The chlorophyll content increased with increasing $CaCl_2$ concentration but it tended to decrease when the $CaCl_2$ concentration increased to ≥0.08 M.

EVALUATION EXAMPLE 4: EVALUATION OF FAME CONTENTS

Figure 6:
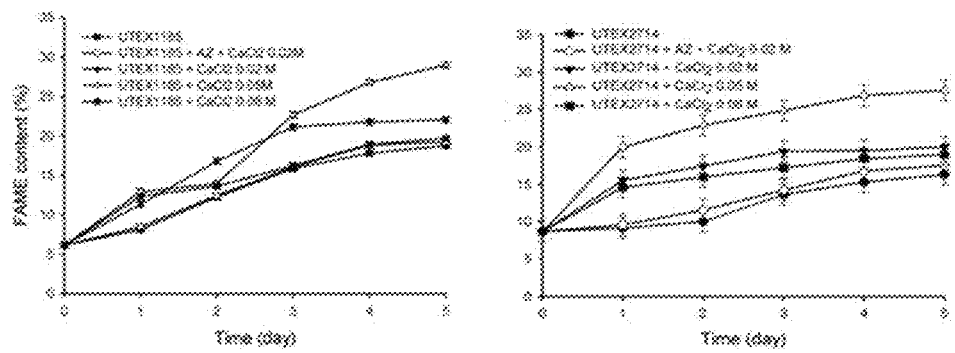
FIG. 6 shows the contents (%) of fatty acid methyl esters (FAMEs) in biomasses produced in Example 3 and Comparative Example 1.

FIG. 6 shows the contents (%) of fatty acid methyl esters (FAMEs) in the biomasses produced in Example 3 and Comparative Example 1.

The contents of FAMEs in the samples of Example 3 and Comparative Example 1 were measured by chromatography. In FIG. 6, UTEX1185 and UTEX2714 indicate *Neochloris oleoabundans* and *Chlorella sorokiniana*, respectively.

The results reveal that the contents of FAMEs in the samples of Example 3 were higher than those in the samples of Comparative Example 1. The highest FAME content was observed when 0.05 M $CaCl_2$ was added.

The highest FAME productivity (mg/L/day) and the highest lipid content (%) were also measured when 0.05 M $CaCl_2$ was added.

EVALUATION EXAMPLE 5: EVALUATION OF CALCITE PRODUCTIVITIES

Figure 7:
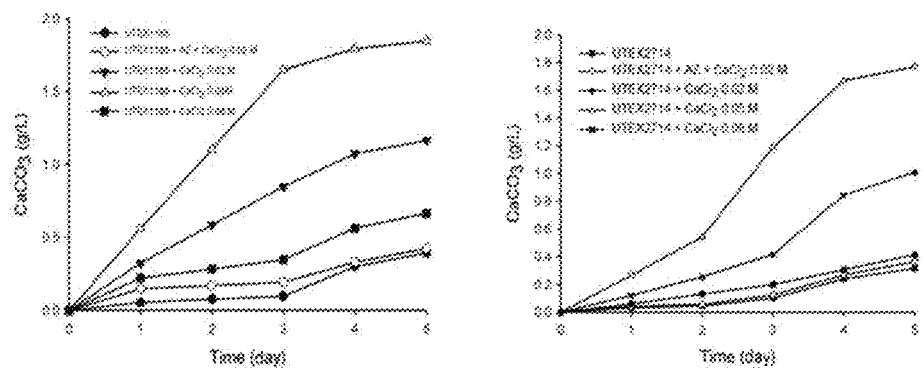
FIG. 7 shows calcite productivities in Example 3 and Comparative Example 1.

FIG. 7 shows calcite productivities in Example 3 and Comparative Example 1.

As in Evaluation Example 3, calcite productivities were measured for the samples of Example 3 and Comparative Example 1. The largest amount of calcite was produced when 0.05 M $CaCl_2$ was added. The calcite productivities when *Neochloris oleoabundans* was used were higher than those when *Chlorella sorokiniana* was used.

EVALUATION EXAMPLE 6: EVALUATION OF CARBON DIOXIDE REDUCTION RATES

The reduction rates of carbon dioxide were measured for the samples of Examples 2-3 and Comparative Example 1. As a result, when *Neochloris oleoabundans* was used in Examples 2-3, the carbon dioxide reduction rate was found to be 1.3 g/l/day, which was 1.32 times higher than the carbon dioxide reduction rate measured in Comparative Example 1. The production of calcite achieved an additional carbon dioxide reduction rate of 0.17 g/l/day. In addition, when *Chlorella sorokiniana* was used in Examples 2-3, the carbon dioxide reduction rate was found to be 1.13 g/l/day, which was 1.32 times higher than the carbon dioxide reduction rate measured in Comparative Example 1. The production of calcite achieved an additional carbon dioxide reduction rate of 0.16 g/l/day. Particularly, the highest carbon dioxide reduction rate was found when 0.05 M $CaCl_2$ was added.

EVALUATION EXAMPLE 7: EVALUATION OF AMOUNTS OF OXYGEN RELEASED

Figure 8:
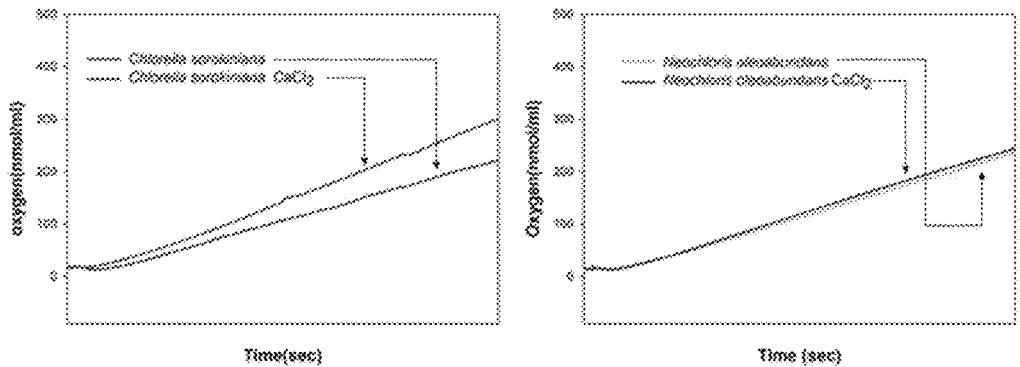
FIG. 8 shows the amounts of oxygen released in Examples 3 and 4 and Comparative Example 1.

FIG. 8 shows the amounts of oxygen released in Examples 3 and 4 and Comparative Example 1.

The amounts of oxygen released were measured using $O_2$ electrodes for the samples of Examples 2-3 and Comparative Example 1. The amounts of oxygen released were used to determine the photosynthesis efficiencies of the microalgal species. As a result, higher photosynthesis efficiencies were observed in the calcite-containing samples.

EVALUATION EXAMPLE 8: EVALUATION OF INDUCTION OF BIOMINERALIZATION AND CHEMICAL MINERALIZATION

Figure 9:
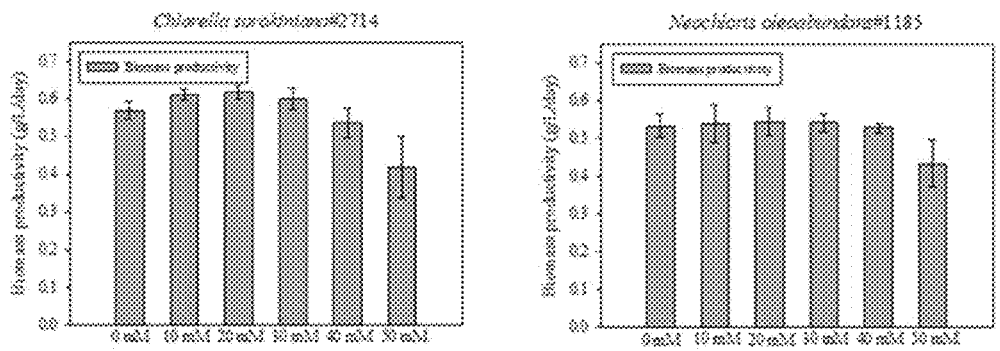
FIG. 9 shows biomass productivities with varying concentrations of a basic solution in Example 4.
Figure 10:
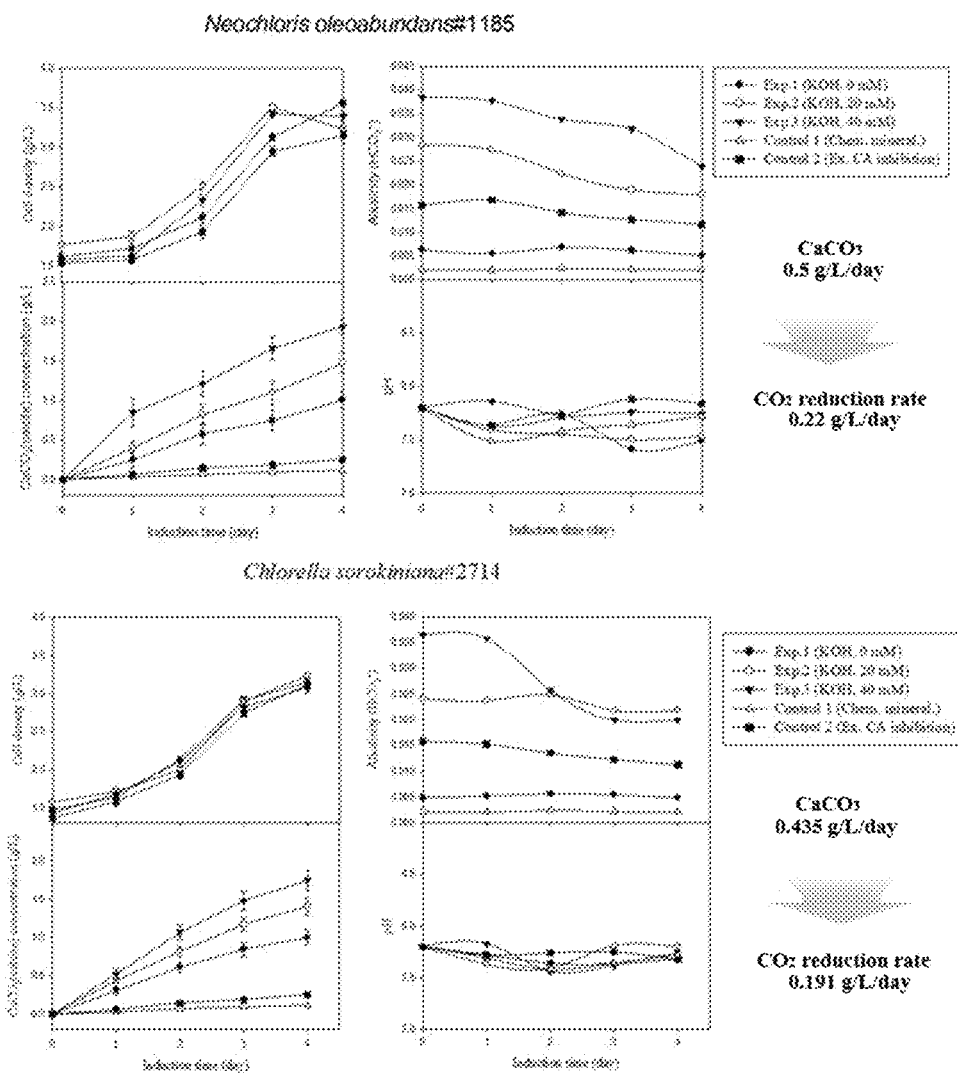
FIG. 10 shows cell densities, alkalinities, calcite ($CaCO_3$) concentrations, and pH values in Example 4.

FIG. 9 shows biomass productivities with varying concentrations of the basic solution in Example 4 and FIG. 10 shows cell densities, alkalinities, calcite ($CaCO_3$) concentrations, and pH values in Example 4.

Biomass productivities, cell densities, alkalinities, calcite concentrations, pH values, and carbon dioxide reduction rates were measured with increasing concentration of the KOH aqueous solution by 10 mM in Example 4. In FIG. 10, Control 1 was the experimental group where chemical mineralization was induced but biomineralization was not induced, and Control 2 was the experimental group where acetazolamide as a biomineralization inhibitor was used.

Referring to FIG. 9, the biomass productivities measured after secondary supply of the aqueous KOH solution were high compared to those measured before secondary supply of the aqueous KOH solution (i.e. 0 mM KOH). However, the biomass productivity began to decrease from when the concentration of the aqueous KOH solution exceeded 40 mM.

Referring to FIG. 10, only biomineralization was induced when the concentration of the aqueous KOH solution was 20 mM but chemical mineralization as well as biomineralization was induced when the concentration of the aqueous KOH solution was 40 mM. These results demonstrate that the simultaneous induction of chemical mineralization and biomineralization leads to a minimal loss of biomass, enabling the production of a larger amount of calcite and an increase in the reduction rate of carbon dioxide.

Although the present invention has been described herein with reference to the specific embodiments, these embodiments do not serve to limit the invention and are set forth for illustrative purposes. It will be apparent to those skilled in the art that modifications and improvements can be made without departing from the spirit and scope of the invention. Such simple modifications and improvements of the present invention belong to the scope of the present invention, and the specific scope of the present invention will be clearly defined by the appended claims.

What is claimed is:

1. A method for carbon resource utilization comprising:
   (a) supplying carbon dioxide to a medium to form bicarbonate ions ($HCO_3^-$);
   (b) inoculating one or more microalgal species into the medium, followed by photo-culture;
   (c) supplying calcium ions ($Ca^{2+}$) to the medium;
   (d) primarily supplying a first basic solution to maintain pH of the medium at 7.5 to 8.5 such that biomineralization is induced, after supply of the calcium ions in step (c); and
   (e) secondarily supplying a second basic solution to induce both biomineralization and chemical mineralization after the primarily supplying the basic solution, wherein the one or more microalgal species are photo-cultured, to produce calcite ($CaCO_3$)-containing biomass.

2. The method according to claim 1, wherein the calcium ions are bound to cell walls of the one or more microalgal species and react with the bicarbonate ions to produce calcite, and the one or more microalgal species adhere to one another through nonpolar covalent bonds between calcite particles to produce biomass.

3. The method according to claim 1, further comprising supplying a third basic solution to the medium to maintain the pH of the medium at 7.0 to 8.5 between steps (a) and (b).

4. The method according to claim 3, wherein the third basic solution is an 8 to 10 mM aqueous potassium hydroxide (KOH) solution.

5. The method according to claim 3, wherein the third basic solution is a solution of at least one base selected from the group consisting of sodium hydroxide (NaOH), potassium hydroxide (KOH), ammonia ($NH_4OH$), calcium hydroxide ($Ca(OH)_2$), and magnesium hydroxide ($Mg(OH)_2$).

6. The method according to claim 1, wherein the one or more microalgal species are selected from the group consisting of *Chlorella vulgaris, Chlorella sorokiniana, Spirulina* sp., *Dunaliella* sp., *Haematococcus pluvialis, Schizochytrium* sp., *Crypthecodinium* sp., *Chlamydomonas* sp., *Neochloris* sp., *Aphanizomenon* sp., and *Cyanobacterium* sp.

7. The method according to claim 1, further comprising stopping the supplying the carbon dioxide to the medium to flocculate and collect the biomass after step (c).

8. The method according to claim 1, wherein the calcium ions are supplied by adding an aqueous calcium chloride ($CaCl_2$) solution to the medium.

9. The method according to claim 8, wherein the aqueous calcium chloride solution has a concentration of 0.03 to 0.06 M.

10. The method according to claim 1, wherein the first basic solution is an aqueous potassium hydroxide (KOH) solution having a concentration not higher than 20 mM.

11. The method according to claim 1, wherein the second basic solution is an aqueous potassium hydroxide (KOH) solution having a concentration not higher than 40 mM.

12. The method according to claim 1, wherein step (c) is carried out when the one or more microalgal species are photo-cultured to a density of at least 1.0 g/l.

13. The method according to claim 1, wherein the calcite comprises nanoparticles.

\* \* \* \* \*